(12) United States Patent  
Mirlay (10) Patent No.: US 8,920,495 B2  
(45) Date of Patent: Dec. 30, 2014

(54) INTRAOCULAR LENS (IOL) WITH MULTI OPTICS ASSEMBLY

(76) Inventor: Ram Srikanth Mirlay, Karnataka (IN)

( * ) Notice: Subject to any disclaimer, the term of this patent is extended or adjusted under 35 U.S.C. 154(b) by 88 days.

(21) Appl. No.: 13/703,275

(22) PCT Filed: May 16, 2011

(86) PCT No.: PCT/IN2011/000339  
§ 371 (c)(1),  
(2), (4) Date: Jan. 30, 2013

(87) PCT Pub. No.: WO2011/154972  
PCT Pub. Date: Dec. 15, 2011

(65) Prior Publication Data  
US 2013/0131796 A1    May 23, 2013

(30) Foreign Application Priority Data

Jun. 10, 2010  (IN) ........................... 1608/CHE/2010  
Jun. 10, 2010  (IN) ........................... 1609/CHE/2010

(51) Int. Cl.  
*A61F 2/16*    (2006.01)

(52) U.S. Cl.  
USPC ........................................... 623/6.34

(58) Field of Classification Search  
USPC .............. 623/6.34, 6.37–6.4, 6.43, 6.46, 6.49  
See application file for complete search history.

(56) References Cited

U.S. PATENT DOCUMENTS

2006/0184244 A1    8/2006  Evans et al.

FOREIGN PATENT DOCUMENTS

| CN | 1087505 A | 6/1994 |
|---|---|---|
| CN | 101534749 | 9/2009 |
| EP | 0949529 | 10/1999 |

OTHER PUBLICATIONS

International Search Report for International Application No. PCT/IN2011/000339 mailed Nov. 10, 2011.

*Primary Examiner* — Howie Matthews  
(74) *Attorney, Agent, or Firm* — Pearl Cohen Zedek Latzer Baratz LLP (57) ABSTRACT

The various embodiments of the present invention provide a multi-optics intraocular lens (IOL) scaffold assembly for incorporation into a capsular bag of an eye of a subject, provided with a ring platform and a protective umbrella. Several anterior and posterior ribs are hinged to the ring platform to support a posterior lens and an anterior lens. The dynamic spring elastic junctions are provided between the anterior and posterior ribs. The pendulum IOL assembly of the multi-optics intraocular lens (IOL) scaffold assembly enables a near vision of the objects using an optical system designed for a distance focusing in normal gaze. The pendulum IOL assembly has a posterior lens fixed to an equatorial ring platform and a secondary hanging lens provided with a weight at the lower end to act like a pendulum which swings with the posture of the eye.

17 Claims, 10 Drawing Sheets

INTRAOCULAR LENS (IOL) WITH MULTI OPTICS ASSEMBLY

CROSS-REFERENCE TO RELATED APPLICATIONS

This application is a National Phase Application of PCT International Application No. PCT/IN2011/000339, International Filing Date May 26, 2011, claiming priority of Indian Patent Applications Nos. 1608/CHE/2010, filed Jun. 10, 2010, and 1609/CHE/2010, filed Jun. 10, 2010, which are hereby incorporated by reference.

BACKGROUND

1. Technical field

The embodiments herein generally relate to ophthalmic lenses and particularly to an implantable intra ocular lens to be implanted in a mammalian eye. The embodiments herein more particularly relates to a multi-optics intraocular lens (IOL) scaffold assembly for incorporation into a capsular bag of the eye, with dynamic junctions to keep an eye capsule of the eye intact and a pendulum intraocular lens assembly to adjust the vision for near and far objects.

2. Description of the Related Art

An intraocular lens (IOL) is an implanted lens in the mammalian eye, usually replacing the existing crystalline lens, if the crystalline lens is clouded over by a cataract or as a form of refractive surgery to change the eye's optical power. It usually consists of a small plastic lens with plastic side struts, called haptics, to hold the lens in place within a capsular bag inside the mammalian eye. IOLs were traditionally made of an inflexible material (Poly methyl methacrylate), although this has largely been superseded by the use of flexible materials. Most IOLs fitted today are fixed monofocal lenses matched to distance vision. However other types of lenses that are available today are multifocal IOLs and adaptive IOLs. The multifocal IOLs provide the patient with multiple-focused vision at far and reading distances and adaptive IOLs provide the patient with limited visual accommodation.

IOL implantation carries several risks associated with eye surgeries, such as infection, lens rotation, inflammation, and night time halos. Also the lens capsule loses its tone and starts collapsing over a period of time. The greatest disadvantage of these IOLs is that they are not able to prevent the loosening of lens capsule. At present, there is no system and method to keep the eye capsule intact. Hence there is a need of a new system to keep the eye lens capsule intact thereby preventing the collapse of the lens capsules.

An Accommodating Lens is a lens that is made to move, adjust or otherwise alter itself to allow for viewing at all distances. Unlike Multi-Focal Lenses, the Accommodating Lens is much more like the natural lens that was removed during cataract surgery. The natural lens has muscles that pull on the lens, altering its shape, which allows the eye to focus. The Accommodating Lens aims to have this same functionality.

A Dual-Optic Lens is a lens that has two optics or lenses. The dual optics lenses are unsuccessful because of their low sensitivity, less visibility and degradative nature. They fail to focus near objects, when required, especially, during reading and writing.

Hence there is need for a twin optics lens system with good focusing power to provide rapid focus of nearby objects efficiently and effectively while reading and writing.

Further there is no system and method presently available to keep the eye capsule intact. Hence there is a further need of a new system to keep the eye lens capsule intact thereby preventing the collapse of the lens capsules.

The above mentioned shortcomings, disadvantages and problems are addressed herein, which will be understood by reading the following specification.

Objects of the Invention

A primary objective of the embodiments herein is to develop a hinged IOL with multi-optics assembly provided with a scaffold structure to maintain the shape of an original natural lens and to keep the eye lens capsule intact in place thereby preventing the collapse of the lens capsule.

Another objective of the embodiments herein is to develop a hinged IOL with multi-optics assembly provided with a scaffold structure to allow a greater freedom for the movement of the optics or lenses with respect to hinge in response to the cilliary body muscle forces.

Yet another objective of the embodiments herein is to develop a hinged IOL with multi-optics assembly provided with a scaffold structure which is impregnated with medications.

Yet another objective of the embodiments herein is to develop a bifocal lens assembly with a pendulum lens which can focus distant and nearby objects easily, efficiently, quickly and particularly for focusing nearby objects especially during reading and writing.

Yet another objective of the embodiments herein is to provide a pendulum lens assembly to enable a weighted lens assembly to move freely and to remain vertical within limits.

Yet another objective of the embodiments herein is to provide a pendulum lens assembly to enable a weighted lens assembly to move freely to increase the distance between two lenses to permit a near focus of an optical system which is designed for distance gaze during a normal gaze (for viewing in the horizontal position of gaze).

These and the other objects and advantages of the embodiments herein will be understood easily by studying the following specification with the accompanying drawings.

SUMMARY

An intraocular lens with multi-optics assembly with a scaffold structure, including a ring platform, a hinge protective umbrella provided to encase and enclose the ring platform, a lens optics including an anterior optical lens and a posterior optical lens, a pluralities of anterior ribs hinged to the ring platform to support the anterior optical lens, a pluralities of posterior ribs hinged to the ring platform to support the posterior optical lens and a pluralities of dynamic elastic spring junctions. The pluralities of the anterior ribs and the pluralities of the posterior ribs are anchored to the ring platform and to the lens optics and fit into a capsular bag of the natural lens during a cataract surgery of a mammalian eye.

According to an embodiment herein, the pluralities of the anterior ribs and the pluralities of the posterior ribs are anchored through a hinge system thereby allowing the pluralities of the anterior ribs, the pluralities of the posterior ribs and the lens optics to move closer and farther from each other.

According to an embodiment herein, the scaffold structure further comprises a plurality of radially arranged thin ribs having a convex shaped outward surface and wherein the plurality of radially arranged thin ribs are spaced apart from each other. A space between the pluralities of radially arranged ribs is open or covered with a medically coated transparent surgical grade material forming a web.

The plurality of anterior ribs and the plurality of posterior ribs are connected to each other by the pluralities of dynamic elastic spring junctions. The plurality of anterior ribs and the plurality of posterior ribs are connected at the hinge so that, the plurality of anterior ribs and the plurality of posterior ribs swivel around the hinge.

According to an embodiment herein, a multi-optics intraocular lens (IOL) scaffold assembly further comprises one or more first sets of ribs lining an anterior capsule and one or more second sets of ribs lining a posterior capsule. The anterior ribs are joined with an anterior ring near the anterior capsule and the posterior ribs are joined with a haptics of an intraocular lens resting on the posterior capsule of the capsular bag. The anterior ring of the scaffold structure holds a single intraocular lens system or a bifocal intraocular lens system or multifocal intraocular system or any other lens system.

According to an embodiment herein, the each of the dynamic elastic spring junction further comprises a rigid rod, an anterior rod and a posterior rod. The anterior rod is connected to the anterior rib and the posterior rod is connected to the posterior rib and wherein the anterior rods and the posterior rods are telescopically coupled to each other.

According to an embodiment herein, a spring is arranged inside a telescoping part to push the posterior rod and the anterior rod away from each other and elastic bands are arranged outside the telescopic part to draw the anterior rods and the posterior rods close to each other. The spring exerts a push force acting outwardly on the anterior rods and the posterior rods and wherein the elastic bands exerts a pull force acting inwardly and wherein the push force exerted by the spring is countered by the pull force of the elastic bands and wherein an outward-pushing vector force of the spring and an inward-pulling vector force of the elastic bands are adjusted unequally so that the outward-pushing vector force of the spring is slightly greater than the inward-pulling vector force of the elastic band in a resting state.

A pendulum lens assembly a multi-optics intraocular lens (IOL) scaffold assembly, including a ring platform, a hinge protective umbrella provided to encase and enclose the ring platform, a lens optics including a secondary optical lens with a weight at the lower end and a posterior optical lens, anterior ribs are hinged to the ring platform to support the anterior optical lens and posterior ribs are hinged to the ring platform to support the posterior optical lens. The anterior ribs and the posterior ribs are anchored to the ring platform and to the lens optics and fit into a capsular bag of the natural lens during a cataract surgery of a mammalian eye.

According to an embodiment herein, the secondary lens is suspended freely with a plurality of threads. The posterior lens and the secondary lens are arranged parallel to each other and close to each other. The Optical axes of the posterior lens and the secondary lens are co-axial when an eye is in a forward gaze. The secondary lens optic axis is aligned to the posterior lens optic axis with a slight off-axis tilt.

According to an embodiment herein, the posterior lens faces downwards along with the eye and the secondary lens moves forwardly towards an anterior capsule thereby increasing a distance between the posterior lens and the secondary lens when the eye is in a downward gaze.

According to an embodiment herein, the ring platform is placed in an equatorial region of the capsular bag and the ring platform is designed to fit and grip the anterior ribs and posterior ribs on the equatorial region. The ring platform further comprises a suspension platform (suspension zone) to support the freely suspended secondary lens. The ring platform further comprises a radially placed plurality of thin ribs attached to the posterior lens on a posterior side and a radically placed plurality of thin ribs attached to an empty ring on an anterior side.

BRIEF DESCRIPTION OF THE DRAWINGS

The other objects, features and advantages will occur to those skilled in the art from the following description of the preferred embodiment and the accompanying drawings in which.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS HEREIN

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

A multi-optics intraocular lens (IOL) scaffold assembly comprises a ring platform with a hinge protective umbrella arranged to encase and enclose the ring platform. A lens optics including an anterior optical lens and a posterior optical lens is supported by the ring platform. Anterior ribs are hinged to the ring platform to support the anterior optical lens and posterior ribs are hinged to the ring platform to support the posterior optical lens. The posterior ribs and the anterior ribs are coupled through a plurality of dynamic elastic spring junctions. The anterior ribs and the posterior ribs are anchored to the ring platform and to the lens optics and fit into a capsular bag of the natural lens during a cataract surgery of a mammalian eye.

According to an embodiment herein, the anterior ribs and the posterior ribs are anchored through a hinge system thereby allowing the anterior ribs, the posterior ribs and the lens optics to move closer and farther from each other.

According to an embodiment herein, a multi-optics intraocular lens (IOL) scaffold assembly further comprises a plurality of radially arranged thin ribs having a convex shaped outward surface and the plurality of radially arranged thin ribs are spaced apart from each other. A space between the pluralities of radically arranged ribs is kept open or covered with a medically coated transparent surgical grade material forming a web.

The anterior ribs and the posterior ribs are connected to each other by dynamic elastic spring junctions. The anterior ribs and the posterior ribs are connected at the hinge so that, the anterior ribs and the posterior ribs swivel around the hinge.

According to an embodiment herein, the a multi-optics intraocular lens (IOL) scaffold assembly further comprises one or more first sets of ribs lining an anterior capsule and one or more second sets of ribs lining a posterior capsule. The anterior ribs are joined with an anterior ring near the anterior capsule of capsular bag of an eye and the posterior ribs are joined with a haptics of an intraocular lens resting on the posterior capsule of the capsular bag. The anterior ring of the holds a mono intraocular lens system or a bifocal intraocular lens system or multifocal intraocular system or any other lens system.

According to an embodiment herein, each of the dynamic elastic spring junctions further comprises a rigid rod, an anterior rod and a posterior rod. The anterior rod is connected to the anterior rib and the posterior rod is connected to the posterior rib. The anterior rods and the posterior rods are coupled telescopically.

According to an embodiment herein, a spring is arranged inside a telescoping part to push the posterior rod and the anterior rod away from each other and elastic bands are arranged outside the telescopic part to draw the anterior rods and the posterior rods close to each other. The spring exerts a push force acting outwardly on the anterior rods and the posterior rods. The elastic bands exert a pull force acting inwardly and the push force exerted by the spring is countered by the pull force of the elastic bands. An outward-pushing vector force of the spring and an inward-pulling vector force of the elastic bands are adjusted unequally so that the outward-pushing vector force of the spring is slightly greater than the inward-pulling vector force of the elastic band in a resting state.

A pendulum lens assembly for a multi-optics intraocular lens (IOL) scaffold assembly comprises a scaffold structure and a ring platform is provided in the scaffold structure. A hinge protective umbrella is provided to encase and enclose the ring platform. A lens optics including a secondary optical lens with a weight at the lower end and a posterior optical lens is supported by the ring platform. Anterior ribs are hinged to the ring platform to support the secondary optical lens and posterior ribs are hinged to the ring platform to support the posterior optical lens. The anterior ribs and the posterior ribs are anchored to the ring platform and to the lens optics and fit into a capsular bag of the natural lens during a cataract surgery of a mammalian eye.

According to an embodiment herein, the secondary lens is suspended freely with a plurality of threads. The posterior lens and the secondary lens are arranged in parallel to each other and close to each other. The optical axes of the posterior lens and the secondary lens are co-axial when an eye is in a forward gaze. The optical axis of the secondary lens is aligned to the optic axis of the posterior lens with a slight off-axis tilt.

According to an embodiment herein, the posterior lens faces downwards along with the eye and the secondary lens moves forwardly towards an anterior capsule thereby increasing a distance between the posterior lens and the secondary lens, when the eye is in a downward gaze.

According to an embodiment herein, the ring platform is placed in an equatorial region of capsular bag and the ring platform is designed to fit and grip the anterior and posterior ribs on the equatorial region. The ring platform further comprises a suspension platform (suspension zone) to support the freely suspended secondary lens. The ring platform further comprises radially placed plurality of thin ribs attached to the posterior lens on a posterior side and a radially placed plurality of thin ribs attached to an empty ring on an anterior side.

Figure 1A:
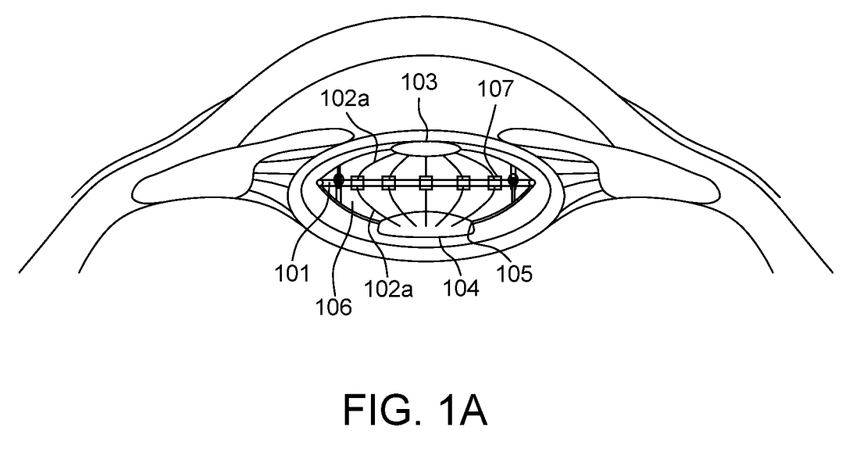
FIG. 1A is a perspective view of a multi-optics intraocular lens (IOL) scaffold assembly for incorporated in a capsular bag of an eye of a subject and FIG. 1B illustrates a side view of a basket scaffolding structure in a hinged IOL with multi-optics assembly, according to one embodiment herein.
Figure 1B:
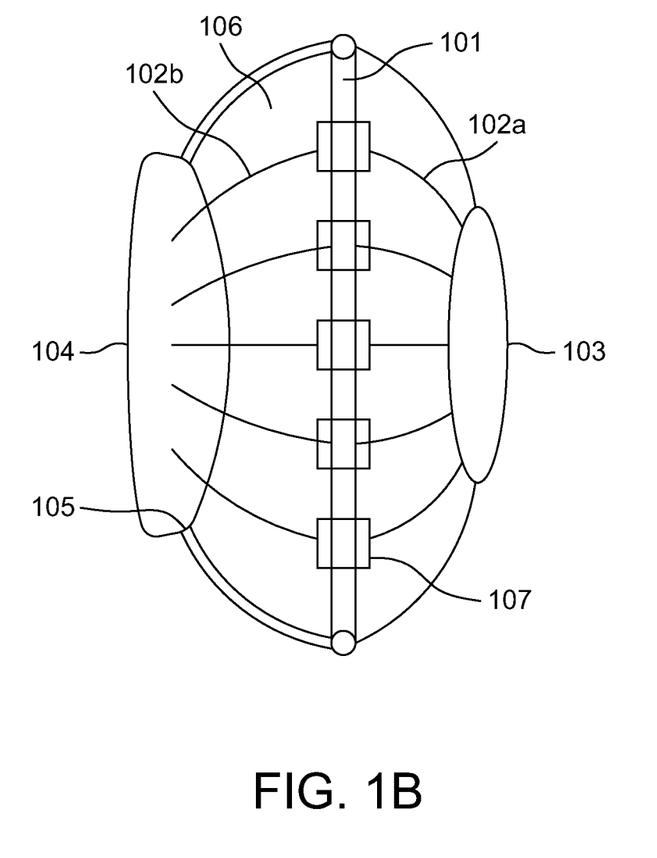

FIG. 1A depicts a perspective view of a multi-optics intraocular lens (IOL) scaffold assembly incorporated in a capsular bag of an eye of a subject. The multi-optics intraocular lens scaffold assembly 106 with an arrangement of ribs 102a and 102b and a ring platform 101, is shown implanted in an eye supporting capsular bag of the eye, as shown in FIG. 1A. FIG. 1B illustrates a side view of a multi-optics intraocular lens (IOL) scaffold assembly, according to one embodiment herein. The IOL scaffold assembly 106 of the present invention comprises a ring platform 101, which is in the form of a thin ring as shown in FIG. 1. Two sets of thin ribs 102a and 102b are extended from the ring platform 101. The two sets of thin ribs 102a and 102b are extended from the ring platform 101 through a hinge system 107. One set of ribs 102a are arranged to support an anterior capsule of a capsular bag of the eye and another set of ribs 102b are arranged to support a posterior capsule of the capsular bag. Anterior ribs 102a meet an anterior ring 103 and posterior ribs 102b meets the haptics of the IOL optic (main optic 104), which rests on the posterior capsule of the lens bag (capsular bag). The anterior ribs 102a and posterior 102b ribs are joined with the ring platform 101 by the respective hinges. The anterior ribs 102a and posterior ribs 102b are arranged radially and have convex structure projecting outwardly. The hinges 107 allow the anterior and posterior ribs 102a and 102b to move closer and farther from each other. Each rib has a square edge 105 design for inhibiting the chance of both posterior and anterior capsular opacification.

According to an embodiment herein, the ring platform 101 has a diameter of 9 to 16 mm and preferably a diameter of 13 mm. The number of anterior ribs 102a and posterior ribs 102b are 4 to 24. The space between the anterior ribs 102a and posterior ribs 102b are kept open or covered with a medically coated transparent surgical grade material, forming a "web".

According to an embodiment herein, the anterior ring 103 has a diameter of at least 5 to 8 mm. The anterior ring is arranged to oppose or abut the anterior capsule (partially or fully) and mounted closely to the approximate position of the rhexsis. The anterior ring 103 of the scaffold structure 106 may hold another optic or lens forming a bifocal IOL system, or it may remain empty, forming a single IOL system. The number of haptics provided in the system is 2 to 8.

Figure 2:
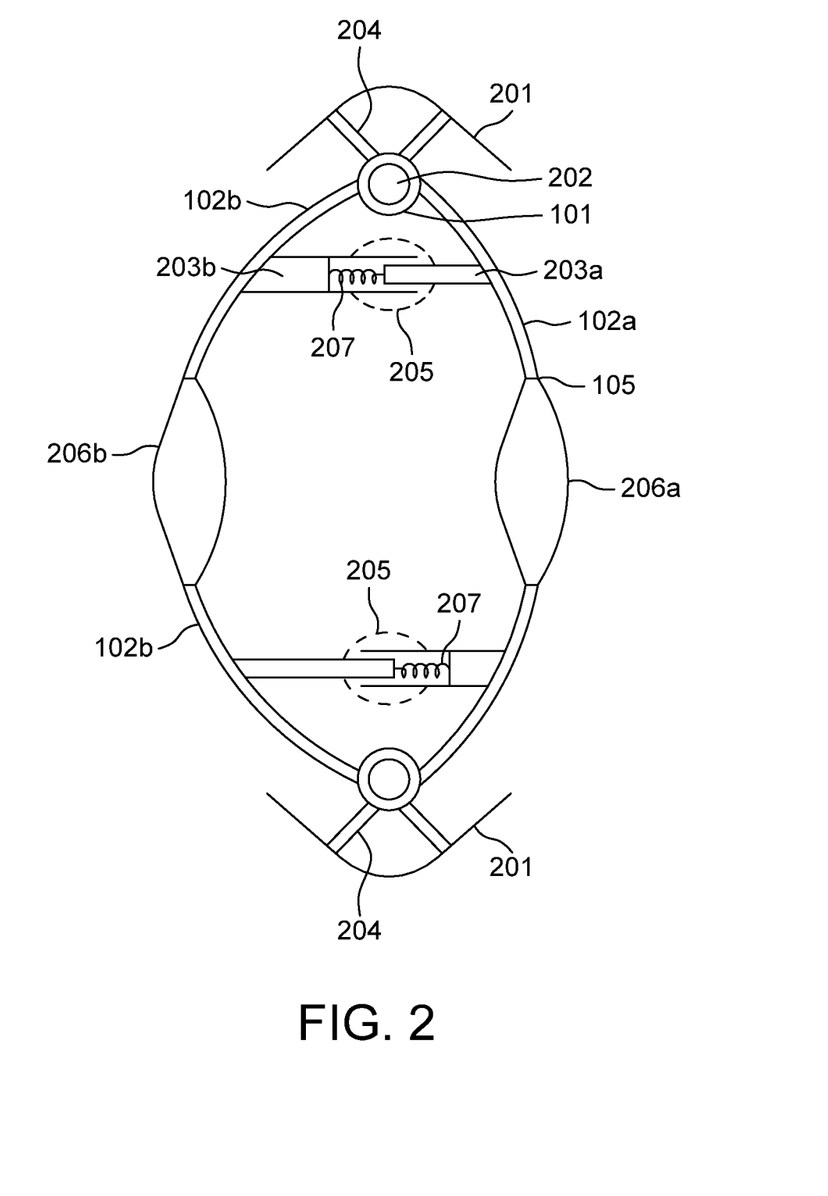
FIG. 2 illustrates a side view of a rib structure in a hinged IOL with multi-optics assembly, according to one embodiment herein.

FIG. 2 illustrates a side view of a rib structure in a hinged IOL with multi optic assembly, according to another embodiment herein. The hinged IOL assembly has a bifocal lens system provided with two optics namely an anterior lens 206a and a posterior lens 206b. They are connected to the ring platform 101 via the anterior ribs 102a and the posterior ribs 102b respectively. A hinge protective umbrella 201 is provided to encase and enclose the ring platform 101. The posterior lens 206b is angulated (vaulted) posteriorly and the anterior lens 206b is vaulted anteriorly.

According to an embodiment herein, the anterior ribs 102a and posterior ribs 102b are connected to each other by a unique dynamic junction, which is a combination of spring 207 and elastic bands 205. The anterior ribs 102a and posterior ribs 102b are also connected at the hinge 202, around which the anterior ribs 102a and posterior ribs 102b swivel. Each rib has a square edge 105 design for inhibiting the chance of both posterior and anterior capsular opacification.

According to an embodiment herein, the unique dynamic junction consists of a rigid rod 204, an anterior rod 203a connected to the anterior rib 102a, and a posterior rod 203b connected to the posterior rib 102b. The anterior rods and the posterior rods are coupled and moved telescopically into each other. A spring 207 is arranged inside the telescoping part and the spring 207 has a tendency to push the anterior rod 203a and the posterior rod 203b away from each other. The hinged IOL assembly also includes one or more elastic bands 205 having a tendency to draw the anterior rods 203a and posterior rods 203b closer to each other. The elastic bands are mounted outside the telescopic junction. Thus the outward push of the spring 207 on the anterior rods 203a and posterior rods 203b is countered by the inward pull of the elastic bands 205. The outward-pushing vector force of the spring 207 and the inward-pulling vector force of the elastic bands 205 are carefully adjusted to be slightly unequal so that in the resting state, the outward push of the spring 207 is slightly greater than the inward pull of the elastic band 205. According to one embodiment of the present invention, reverse adjustments are also made, depending on the vector forces of the ciliary body and zonules.

According to an embodiment herein, the number of the unique dynamic junctions is 2 to 16. The unique dynamic junctions are made up of the same material as the ribs 102a and 102b, but are firm/strong and rigid. The unique dynamic junctions are located at a distance of around 1 mm to 3 mm from the ring platform 101.

According to an embodiment herein, the anterior ribs 102a and the posterior ribs 102b are interconnected with its neighboring ribs via a thin artificial membrane or material, thereby helping in holding the original lens capsule in place and preventing it from shrinking. If desired, the thin artificial membrane or material is medicated with a drug of choice.

According to an embodiment herein, the hinge protective umbrella 201 is provided around the hinges 202 that are arranged in the ring platform 101 in the scaffold structure. The hinge protective umbrella 201 is a 360° protective umbrella, designed to encase the ring platform 101. The hinge protective umbrella 201 fits into the equator to the natural lens bag. The hinge protective umbrella 201 is supported by rods 204 extended from the platform hinge 202. The hinge protective umbrella 201 is made of surgical grade material. The hinge protective umbrella 201 is thin and bends with memory of its original shape. The hinge protective umbrella 201 extends from the equator and stops just away from ring platform 101 to prevent the capsular bag from contracting onto the hinge system 202 and ring platform 101.

According to an embodiment herein, multi-optics intraocular lens (IOL) scaffold assembly includes two lenses, i.e. an anterior lens 206a and a posterior lens 206b. The refractive power of the anterior lens 206a and posterior lens 206b is divided between the ends in an equal or unequal manner. The anterior lens 206a and posterior lens 206b are made up of any surgical grade material. A square shaped posterior edge surface is designed to reduce the chance of posterior capsular opacification. The optics (anterior lens 206a and posterior lens 206b) is mono-focal, bi-focal, or multi-focal. The anterior lens 206a and posterior lens 206b are refractive, diffractive, or a combination of both designs.

Figure 3:
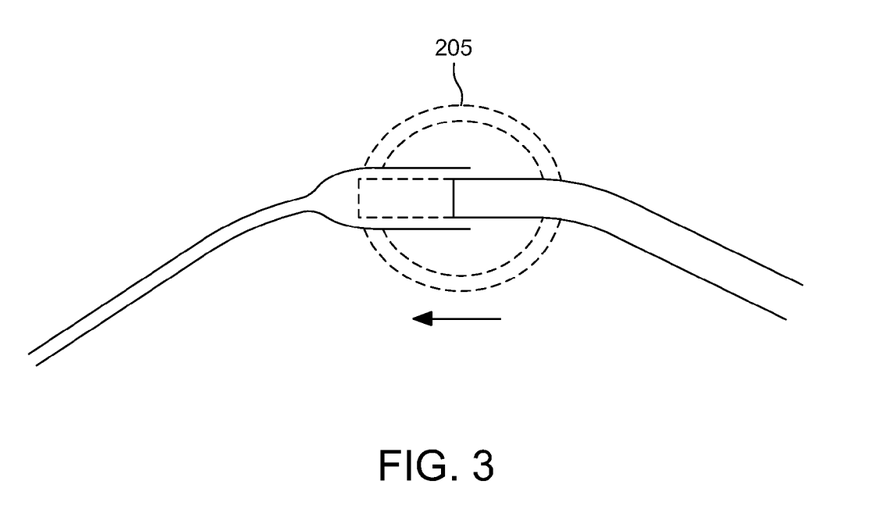
FIG. 3 illustrates a side view of a dynamic junction with thin elastic bands in a hinged IOL with multi-optics assembly, according to one embodiment herein.
Figure 4:
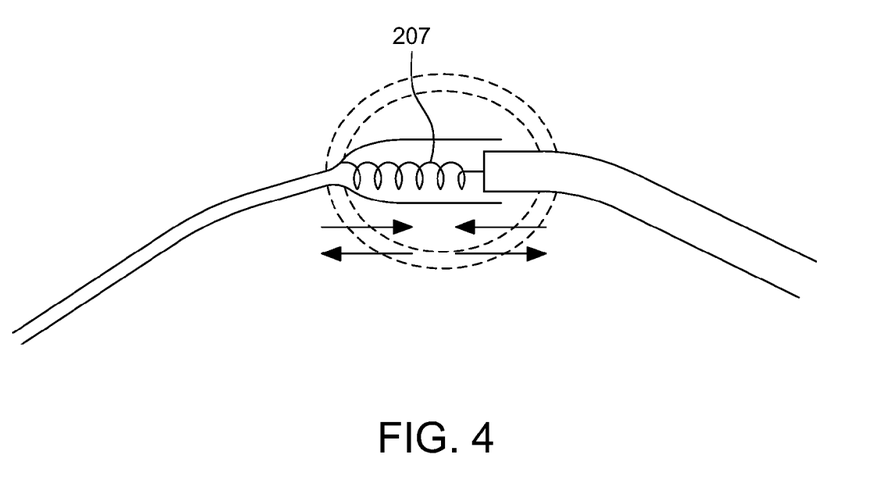
FIG. 4 illustrates a side view of a dynamic junction with the spring in a hinged IOL with multi-optics assembly, according to one embodiment herein.

FIG. 3 illustrates a side view of the unique dynamic junction with thin elastic bands of the multi-optics intraocular lens (IOL) scaffold assembly, according to one embodiment herein while FIG. 4 illustrates a side view of the unique dynamic junction with the spring of the multi-optics intraocular lens (IOL) scaffold assembly, according to one embodiment of the present invention. With respect to FIG. 3 and FIG. 4, the unique dynamic junction consists of a rigid rod, an anterior rod and a posterior rod. The anterior rod is connected to an anterior rib and the posterior rod is connected to a posterior rib. The anterior rod and the posterior rod are coupled telescopically into each other as shown in FIG. 2. A spring 207 (FIG. 4) is provided inside the telescoping part with a tendency to push the anterior rod and posterior rod away from each other as shown in FIG. 4. The elastic bands 205 are arranged outside the telescopic junction with a tendency to draw the anterior rod and posterior rod closer to each other as shown in FIG. 3.

The "push" force acting outwardly of the spring 207 (FIG. 4) on the rods (anterior rod and posterior rod) is countered by the "pull" force acting inwardly of the elastic bands 205 (FIG. 3). The outward-pushing vector force of the spring 207 (FIG. 4) and the inward-pulling vector force of the elastic bands 205 (FIG. 3) are carefully adjusted to be slightly unequal so that the outward-pushing force of the spring 207 (FIG. 4) is slightly greater than the inward-pulling force of the elastic band 205 (FIG. 3) in the rest state. The reverse adjustments are also made, depending on the vector forces of the ciliary body and zonules.

Figure 5:
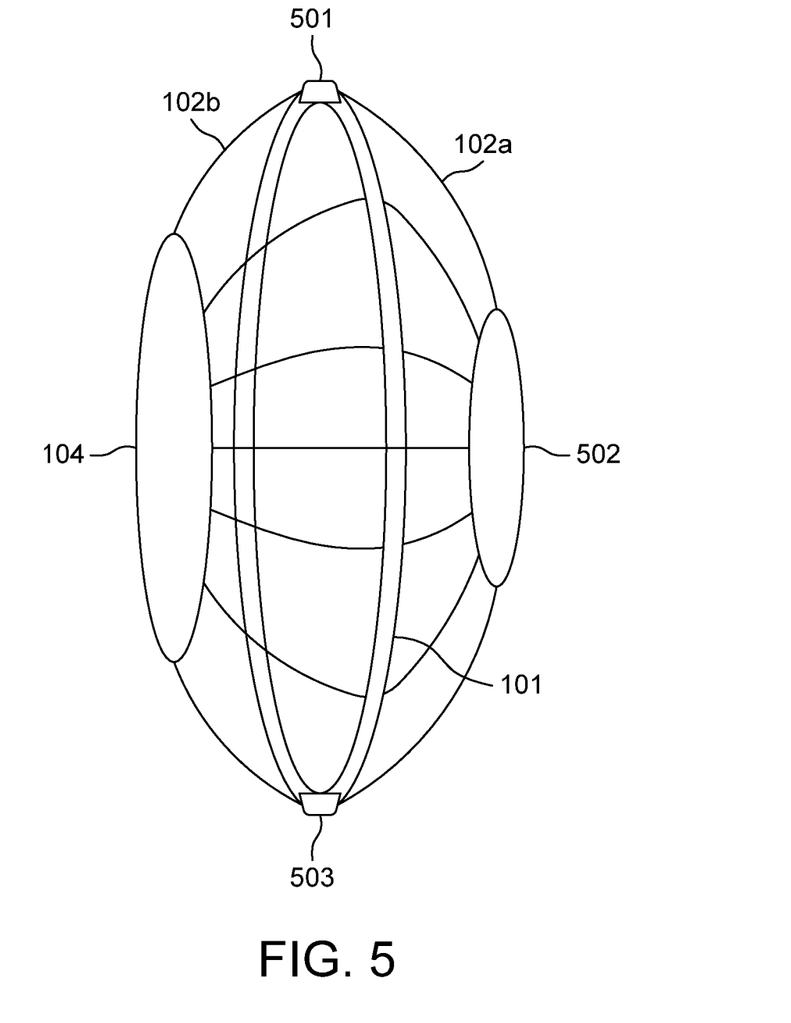
FIG. 5 illustrates a side view of a scaffolding structure design for the pendulum intraocular lens assembly, according to one embodiment herein.

FIG. 5 illustrates a side view of a scaffolding structure design for the pendulum intraocular lens assembly, according to one embodiment herein. The pendulum IOL assembly includes a circular ring called the ring platform 101, which lines the equator of a lens capsule. Posterior scaffolding ribs 102b radiate outwardly from the ring platform 101 and get attached to the main posterior lens 104 on the posterior side. Similarly the anterior scaffolding ribs 102a radiate outwardly from the ring platform 101 and get attached to an empty ring 502 on the anterior side. The anterior scaffolding ribs 102a and the posterior scaffolding ribs 102b are thin ribs. The ring platform 101 of the present invention has a platform 501 at 12 O'clock position and a platform 503 6 O'clock position. The ring platform 501 at 12 O'clock position helps to suspend the pendulum optic, which is also known as secondary lens.

Figure 6:
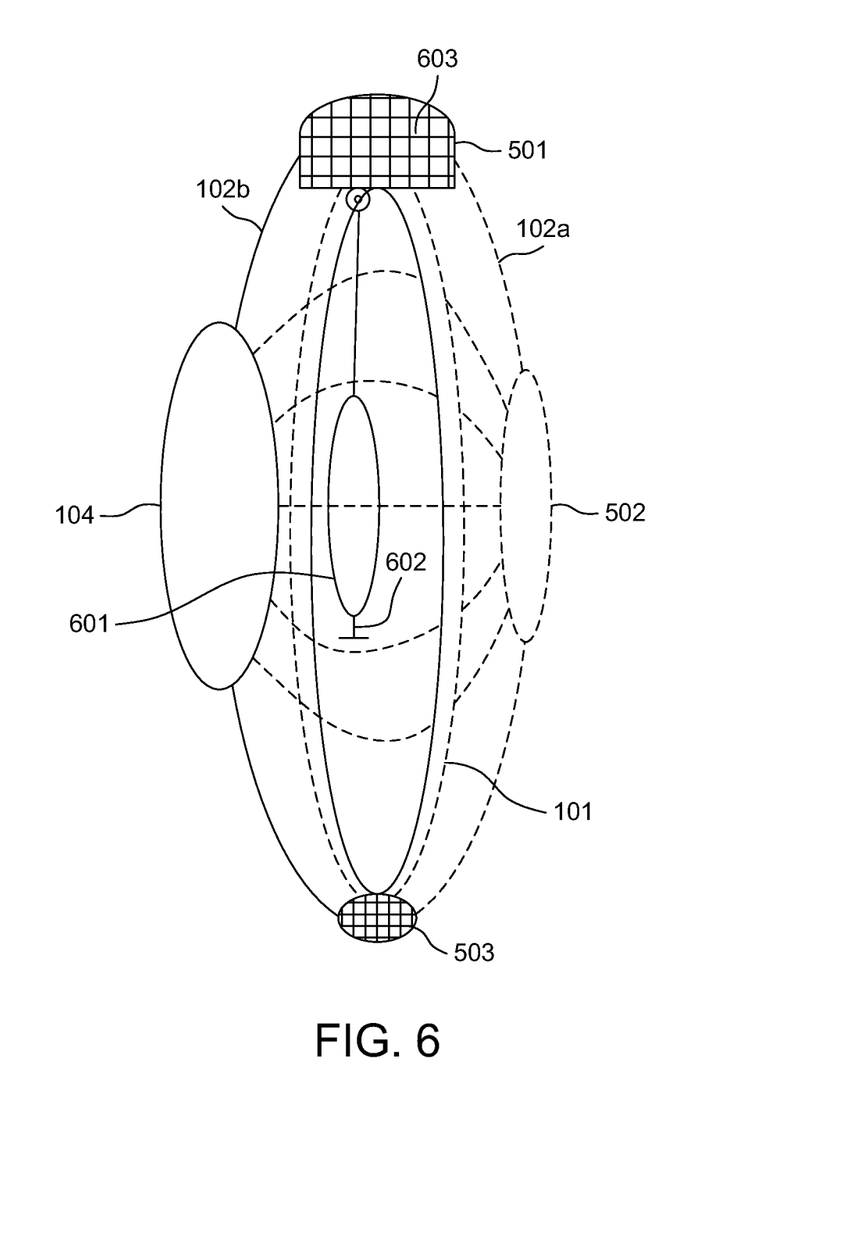
FIG. 6 illustrates a side view of the pendulum intraocular lens assembly, according to one embodiment herein.

FIG. 6 illustrates a side view of the pendulum intraocular lens assembly according to one embodiment herein. The pendulum IOL assembly is placed within the scaffold structure as shown in FIG. 5. The main optic 104 is held by the posterior ribs in the posterior region of the capsule. The main optic 104 is arranged on the ring platform 501 at 12 O'clock position, as shown in FIG. 5. The secondary optic 601 is hung like a pendulum with a weight 602 attached to its lower surface. The ring platform 501 at 12 O'clock position has a hinge system 603. The optic 104 is also connected to the ring platform 503 arranged at 6 O'clock position.

Figure 7:
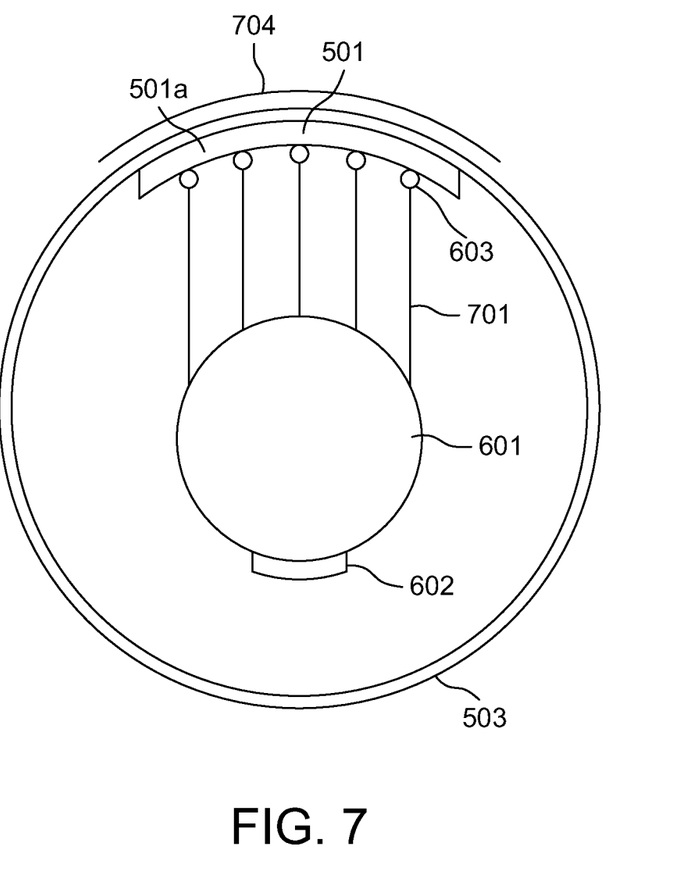
FIG. 7 illustrates a front view of the pendulum intraocular lens assembly indicating a suspension zone and the secondary lens (optic) only, according to one embodiment herein.

FIG. 7 illustrates a front view of the pendulum intraocular lens assembly indicating a suspension zone and the secondary lens (optic) only, according to one embodiment herein. The pendulum IOL further includes a suspension zone (hinge) 501a which is centered on the 12 O'clock position 501 as shown in FIG. 7. The suspension zone 501a has suspension threads 701 which support the free hanging secondary optic 601 with the weight 602 below. The length of the suspension threads 701 is adjusted to ensure the accurate centering of the secondary optic 601. The suspension threads 701 are connected to the suspension zone 501a through a hinge system 603. The ring platform 101 of the present invention has platform 501 at 12 O'clock position as shown in FIG. 7. A protective umbrella 704 is adopted to partially encase and enclose the ring platform as shown in FIG. 7.

Figure 8:
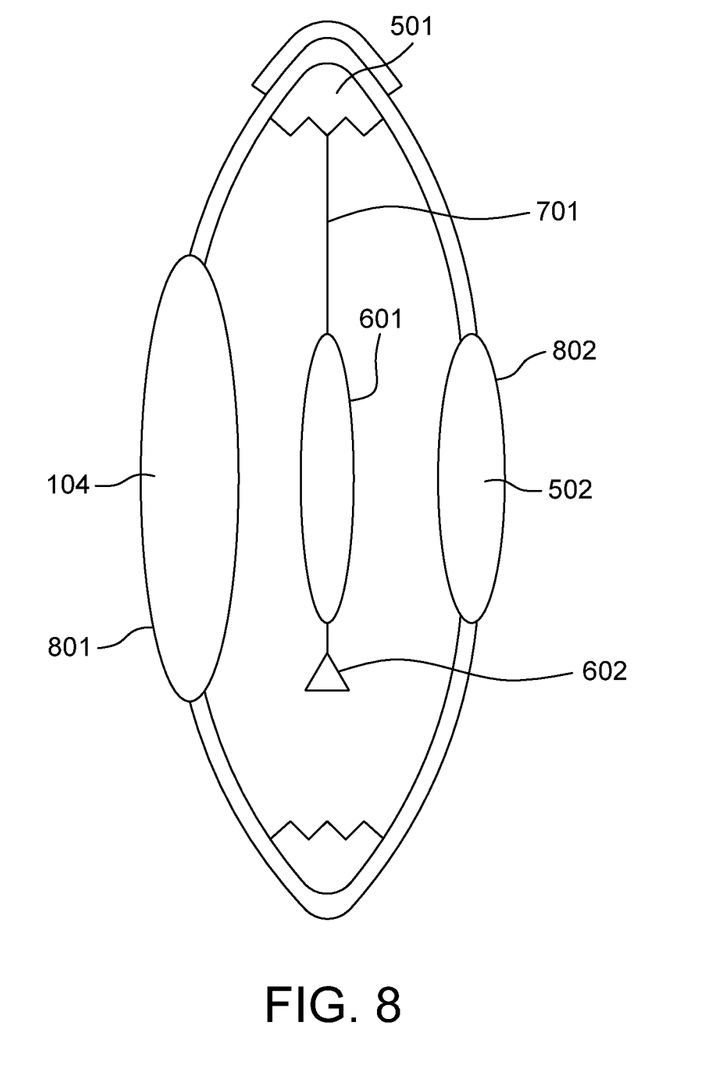
FIG. 8 illustrates a side view of the pendulum intraocular lens assembly in normal condition, according to one embodiment herein.

FIG. 8 illustrates a side view of the pendulum intraocular lens assembly in normal condition, according to one embodiment herein. The main optic 104 (posterior lens) of the posterior capsule 801 faces straight or downwards along with an eye. The freely suspended pendulum optic 601 (secondary lens) along with weight 602 from the ring platform 501 arranged at 12 O'clock position, by a suspension thread 701 aligns with the main optic 104 (posterior lens) during the normal condition and moves forward towards the anterior capsule 802 provided with an empty ring 502 during down gaze for near focus due to the gravity effect on its weight 602 thereby increasing or decreasing the distance between the two optics (posterior lens 104 and secondary lens 601). The power of the secondary optic 601 is so adjusted that the increased distance creates an additional power of +2.5 to +4.0 diopters to enable a near focusing capacity for the pendulum intraocular lens system.

Figure 9:
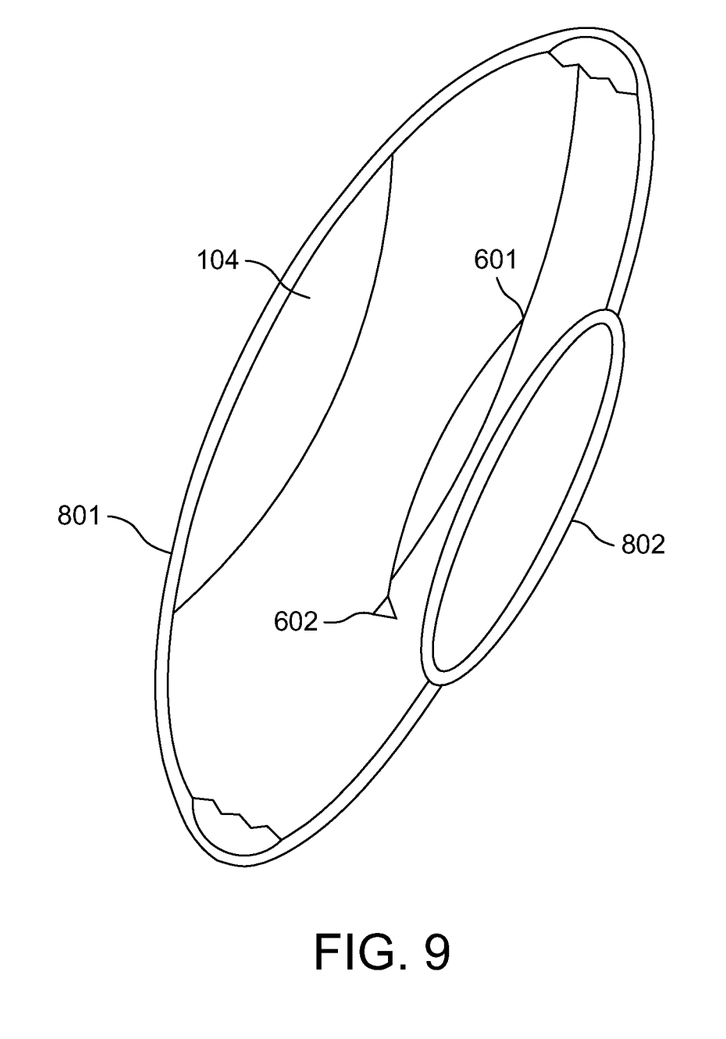
FIG. 9 illustrates a side view of the pendulum intraocular lens assembly in down gaze for near focus, according to one embodiment herein.

FIG. 9 illustrates a side view of the pendulum intraocular lens assembly in down-gaze position for near focus, according to one embodiment herein. With respect to FIG. 9, the main optic 104 (posterior lens) of the posterior capsule 801 faces downwards along with an eye. The freely suspended pendulum optic 601 (secondary lens) along with weight 602 moves forward, towards the anterior capsule 802, due to gravity effect of its weight 602. This increases the distance between the two optics (posterior lens 104 and secondary lens 601). The power of the secondary optic 601 is so adjusted that the increased distance creates an additional power of +2.5 to +4.0 diopters to enable a near focusing capacity for the pendulum intraocular lens system.

When the eye is in forward gaze, the posterior lens 104 and the secondary lens 601 (pendulum optics) remain parallel and closest to each other and their optic axis enabling a focusing of distant objects.

Figure 10:
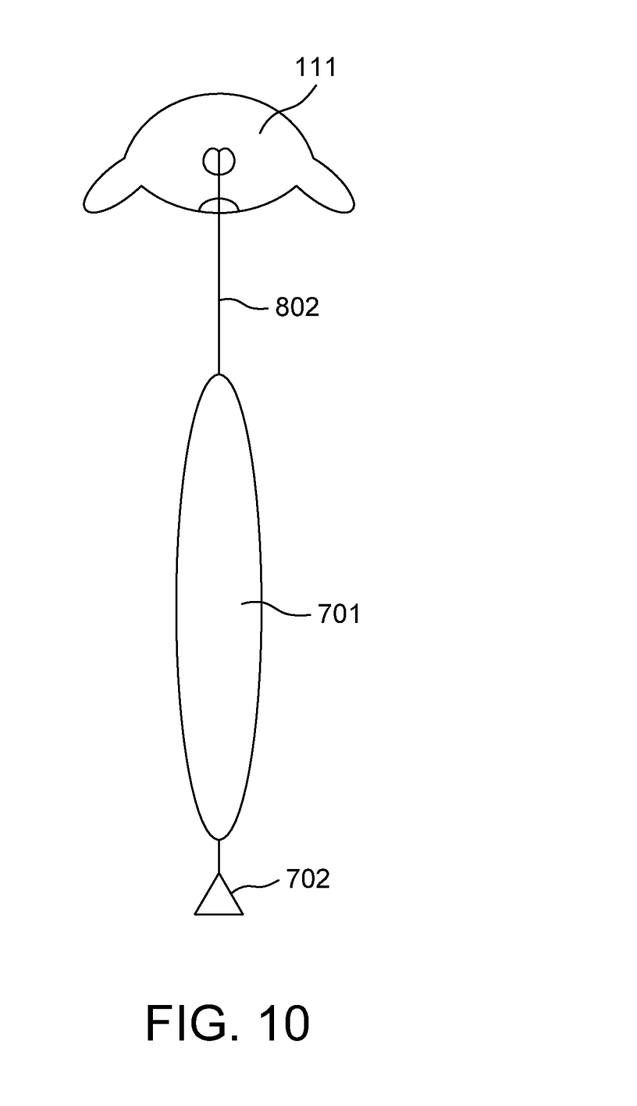
FIG. 10 illustrates a side view of the pendulum lens held by a knob, according to one embodiment herein.

FIG. 10 illustrates a side view of the pendulum lens held by a knob 111, according to one embodiment herein. With respect to FIG. 10, the pendulum lens 601 (secondary lens) with a weight 602 is supported from the ring platform through a knob 111 and the expansion thread 701 to enable a rotatory movement about the axis.

The various embodiments of the present invention provide a scaffolding structure which prevents the lens capsule from collapsing and maintains the shape of the capsule. The present invention provides a multi-optics lens assembly providing monofocal or bifocal lens system. The present invention provides a multi-optics lens assembly which is adjusted by moving under the cilliary forces thereby enabling the focusing of various objects. The present invention provides a multi-optics lens assembly with dynamic elastic junctions so that the outward pull of dynamic elastic junctions keeps the capsule bag rigid. The present invention provides a multi-optics lens assembly with a 360° protective umbrella to prevent the capsular bag from contracting onto the hinge system and the platform ring.

The pendulum lens assembly of the present invention allows a focusing of the lens towards the near objects during reading and writing using a lens system designed for a distant focus. The lens assembly of the present invention has a scaffolding structure to keep the capsular bag housing the lenses intact and rigid. The lenses are provided with an anterior inflammatory chemical coating so that the molecules are absorbed for restarting posterior and anterior capsular specification and during the contraction. Each rib has a square shaped edge design for inhibiting the chance of both posterior and anterior capsular opacification.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

The invention claimed is:

1. A multi-optics intraocular lens (IOL) scaffold assembly for incorporation into a capsular bag of an eye of a subject, comprising:
    an anterior ring with an anterior optical lens configured to be disposed in the anterior region of the capsular bag;
    a posterior optical lens configured to be disposed in the posterior region of the capsular bag;
    a plurality of movable anterior and posterior ribs configured to extend radially from the anterior ring and the posterior optical lens, and anchored to a ring platform, through a plurality of hinges;
    a hinge protective umbrella configured to enclose the ring platform; and
    a plurality of dynamic elastic spring junctions operably connected to the anterior and posterior ribs.

2. The IOL scaffold assembly according to claim 1, wherein the anterior ribs and posterior ribs are anchored to the ring platform and configured to move the anterior and posterior ribs farther from and closer to each other.

3. The IOL scaffold assembly according to claim 1, wherein the anterior and posterior ribs are convex with intervening spaces.

4. The IOL scaffold assembly according to claim 1, wherein the anterior and posterior ribs are covered with webs that are medically coated and are made of transparent surgical grade material.

5. The IOL scaffold assembly according to claim 1, wherein the anterior ribs and the posterior ribs are pivoted to the plurality of hinges for swiveling action.

6. The IOL scaffold assembly according to claim 1, wherein the anterior lens is a single intraocular lens, bi-focal intraocular lens or a multi-focal intraocular lens.

7. The IOL scaffold assembly according to claim 1, wherein the ring platform is disposed at the equatorial region of the capsular bag to support the anterior and posterior ribs.

8. The IOL scaffold assembly according to claim 1, wherein the plurality of dynamic elastic spring junctions comprises:
   a rod;
   an anterior rod; and
   a posterior rod;
   wherein the anterior rod is connected to an anterior rib and the posterior rod is connected to a posterior rib and wherein the anterior rod and the posterior rod are telescopically coupled to each other.

9. The IOL scaffold assembly according claim 8, wherein a spring is disposed internally to connect the anterior and posterior rods, wherein said spring is configured to push the posterior rods and the anterior rods away from each other.

10. The IOL scaffold assembly according to claim 8, wherein a plurality of elastic bands are disposed externally to connect the anterior and posterior rods, wherein said elastic bands are configured to draw the anterior rods and the posterior rods close to each other.

11. An multi-focus intraocular lens (IOL) scaffold assembly for incorporation into a capsular bag of an eye of a subject:
   (a) an anterior ring with an anterior optical lens configured to be disposed in the anterior region of the capsular bag;
   (b) a posterior optical lens configured to be disposed in the posterior region of the capsular bag;
   (c) a plurality of movable anterior and posterior ribs configured to extend radially from the anterior ring and the posterior optical lens, and anchored to a ring platform;
   (d) a suspension platform connected to the ring platform; and
   (e) a movable and weighted secondary lens suspended from the suspension platform and disposed in between the posterior lens and the anterior ring.

12. The IOL scaffold assembly according to claim 11, wherein the secondary lens is suspended freely with a plurality of threads.

13. The IOL scaffold assembly according to claim 11, wherein the posterior lens and the secondary lens are parallel and close to each other and the optical axes of the posterior lens and the secondary lens are co-axial when the eye is in a forward gaze position.

14. The IOL scaffold assembly according to claim 11, wherein the posterior lens and the secondary lens are angled and farther from each other when the eye is in downward gaze position.

15. The IOL scaffold assembly according to claim 11, wherein the optical axis of the secondary lens is aligned relative to the optic axis of the posterior lens with an off-axis tilt.

16. The IOL scaffold assembly according to claim 11, wherein the ring platform is configured to be placed in an equatorial region of the capsular bag and wherein the ring platform is configured to fit and grip the anterior capsule and a posterior capsule on the equatorial region.

17. The IOL scaffold assembly according to claim 11, wherein a rotatable, movable and weighted secondary lens is suspended from a knob of the ring platform by an extendable thread and disposed in between the posterior lens and the anterior ring.

* * * * *